US00PP18727P2

(12) United States Plant Patent
Probst

(10) Patent No.: US PP18,727 P2
(45) Date of Patent: Apr. 15, 2008

(54) ***TRICYRTIS* PLANT NAMED 'TAIPEI SILK'**

(50) Latin Name: *Tricyrtis hybrida*
Varietal Denomination: Taipei Silk

(76) Inventor: Darrell R. Probst, 63 Williamsville Rd., Hubbardston, MA (US) 01452-1315

( * ) Notice: Subject to any disclaimer, the term of this patent is extended or adjusted under 35 U.S.C. 154(b) by 246 days.

(21) Appl. No.: 11/324,478

(22) Filed: Dec. 31, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Wendy C. Haas
*Assistant Examiner*—Georgia Helmer
(74) *Attorney, Agent, or Firm*—C. A. Whealy

(57) ABSTRACT

A new and distinct cultivar of *Tricyrtis* plant named 'Taipei Silk', characterized by its upright and outwardly spreading plant habit; freely branching growth habit; glossy dark green-colored foliage; large inflorescences with numerous purple and white-colored flowers; and winter hardy to USDA Zone 6.

2 Drawing Sheets

Botanical designation: *Tricyrtis hybrida.*
Cultivar denomination: 'Taipei Silk'.

BACKGROUND OF THE INVENTION

The present Invention relates to a new and distinct cultivar of *Tricyrtis* plant, botanically known as *Tricyrtis hybrida,* and hereinafter referred to by the name 'Taipei Silk'.

The new *Tricyrtis* is a product of a planned breeding program conducted by the Inventor in Hubbardston, Mass. The objective of the breeding program was to develop new long-flowering and winter-hardy *Tricyrtis* cultivars with strong foliage and large inflorescences with attractive flowers.

The new *Tricyrtis* originated from a cross-pollination made by the Inventor in 1992 in Hubbardston, Mass. of an unnamed selection of *Tricyrtis formosana,* not patented, as the female, or seed, parent with an unnamed selection of *Tricyrtis lasiocarpa,* not patented, as the male, or pollen, parent. The new *Tricyrtis* was discovered and selected by the Inventor in 1993 as a flowering plant within the progeny of the stated cross-pollination in a controlled environment in Hubbardston, Mass.

Asexual reproduction of the new cultivar by cuttings in a controlled environment in Hubbardston, Mass. since 1994 has shown that the unique features of this new *Tricyrtis* are stable and reproduced true to type in successive generations of asexual propagation.

SUMMARY OF THE INVENTION

Plants of the cultivar Taipei Silk have not been observed under all possible environmental conditions. The phenotype may vary somewhat with variations in environment such as temperature and light intensity without, however, any variance in genotype.

The following traits have been repeatedly observed and are determined to be the unique characteristics of 'Taipei Silk'. These characteristics in combination distinguish 'Taipei Silk' as a new and distinct cultivar:

1. Upright and outwardly spreading plant habit.
2. Freely branching growth habit.
3. Glossy dark green-colored foliage.
4. Large inflorescences with numerous purple and white-colored flowers.
5. Winter hardy to USDA Zone 6.

Plants of the new *Tricyrtis* differ from plants of the female parent selection in the following characteristics:

1. Plants of the new *Tricyrtis* have larger inflorescences and are more freely flowering than plants of the female parent selection.
2. Leaves of plants of the new *Tricyrtis* are glossy whereas leaves of plants of the female parent selection are dull and pubescent.
3. Plants of the new *Tricyrtis* and the female parent selection differ in flower color as plants of the female parent selection have pale lavender-colored flowers.

Plants of the new *Tricyrtis* differ from plants of the male parent selection in the following characteristics:

1. Plants of the new *Tricyrtis* have terminal and axillary inflorescences whereas plants of the male parent selection only have a single terminal panicle.
2. Leaves of plants of the new *Tricyrtis* are glossy whereas leaves of plants of the male parent selection are dull.
3. Plants of the new *Tricyrtis* are more winter hardy than plants of the male parent selection.

Plants of the new *Tricyrtis* can be compared to plants of the *Tricyrtis* cultivar Gilty Pleasure, disclosed in U.S. Plant Pat. No. 13,688. Plants of the new *Tricyrtis* differ from plants of the cultivar Gilty Pleasure primarily in leaf coloration as plants of the cultivar Gilty Pleasure have golden yellow-colored leaves.

BRIEF DESCRIPTION OF THE PHOTOGRAPHS

The accompanying colored photographs illustrate the overall appearance of the new *Tricyrtis,* showing the colors as true as it is reasonably possible to obtain in colored reproductions of this type. Colors in the photographs may differ slightly from the color values cited in the detailed botanical description which accurately describe the colors of the new *Tricyrtis*.

The photograph on the first sheet comprises a side perspective view of a typical plant of 'Taipei Silk' grown in an outdoor nursery.

The photograph on the second sheet is a close-up view of typical flowers of 'Taipei Silk'.

DETAILED BOTANICAL DESCRIPTION

The aforementioned photographs, following observations, measurements and values describe plants of the new *Tricyrtis* grown in Lancaster, Pa. in a polyethylene-covered greenhouse during the summer. During the production of the plants, day temperatures ranged from 21° C. to 46° C. and night temperatures ranged from 18° C. to 29° C. Plants used for the photographs and description were about one year old. Color references are made to The Royal Horticultural Society Colour Chart, 1995 Edition, except where general terms of ordinary dictionary significance are used.

Botanical classification: *Tricyrtis hybrida* cultivar Taipei Silk.

Parentage:

*Female parent.*—Unnamed selection of *Tricyrtis formosana,* not patented.

*Male parent.*—Unnamed selection of *Tricyrtis lasiocarpa,* not patented.

Propagation:

*Type.*—By cuttings.

*Time to initiate roots.*—Summer: About 18 days at 29° C. Winter: About 20 days at 21° C.

*Time to produce a rooted young plant.*—Summer: About 25 days at 29° C. Winter: About 35 days at 21° C.

*Root description.*—Fine; white to brownish in color.

*Rooting habit.*—Freely branching.

Plant description:

*Plant/growth habit.*—Upright and outwardly spreading plant habit; vigorous and freely branching growth habit; lateral branches potentially developing at every node.

*Plant height.*—About 25 cm.

*Plant diameter* (*spread*).—About 20 cm.

*Lateral branch description.*—Length: About 25 cm. Diameter: About 4 mm. Internode length: About 2.5 cm. Strength: Strong, flexible. Texture: Smooth, glabrous. Color: Close to 145A.

*Foliage description.*—Arrangement: Alternate, simple; sessile. Length: About 7.5 cm. Width: About 2.4 cm. Shape: Elliptic. Apex: Acute. Base: Clasping. Margin: Entire. Texture, upper and lower surfaces: Smooth, glabrous. Venation pattern: Parallel. Color: Developing and fully expanded foliage, upper surface: Close to 146A to 147A; venation, similar to lamina. Developing and fully expanded foliage, lower surface: Close to 146B to 147B; venation, similar to lamina.

Flower description:

*Flower type/habit.*—Single, star-shaped flowers arranged in large terminal and axillary cymes. Flowers face upright and outward. Freely flowering habit with numerous flowers per inflorescence.

*Fragrance.*—None detected.

*Natural flowering season.*—Continuously flowering at the end of the summer into the autumn in the Northern Hemisphere. Flowers not persistent.

*Postproduction longevity.*—Flowers last about seven to ten days on the plant.

*Flower buds.*—Height: About 1 cm. Diameter: About 6 mm. Shape: Elongated oblong. Color: Close to 185A.

*Flowers.*—Diameter: About 6 cm. Depth: About 2.5 cm.

*Perianth segments.*—Quantity/arrangement: Six tepals per flower; imbricate. Tepal length, inner tepals: About 2.7 cm. Tepal length, outer tepals: About 3 cm. Tepal width, inner tepals: About 1.4 cm. Tepal width, outer tepals: About 7 mm. Tepal shape, inner tepals: Elliptic. Tepal shape, outer tepals: Lanceolate. Tepal apex, inner tepals: Retuse; reflexed. Tepal apex, outer tepals: Acute. Tepal margin: Entire. Tepal texture, upper and lower surfaces: Smooth, glabrous. Inner tepal color: When opening and fully opened, upper surface: Close to 77A to 77B; towards the center, close to 155D. When opening and fully opened, lower surface: Close to 77D. Outer tepal color: When opening and fully opened, upper surface: Close to 155D; towards the apex, 77A to 77B; spots towards the base, close to 59A. When opening and fully opened, lower surface: Close to 155D.

*Pedicels.*—Angle: About 45° from vertical. Strength: Strong, flexible. Length: About 3 cm. Diameter: About 3 mm. Texture: Smooth, glabrous. Color: Close to 144A to 146A.

*Reproductive organs.*—Stamens: Quantity per flower: Six. Filament length: About 1 cm. Filament color: Close to 4B, random spots, close to 59A. Anther color: Close to 4A to 4B. Pollen amount: None observed. Pistils: Quantity per flower: One. Pistil length: About 1.2 cm. Style color: Close to 53A. Stigma shape: Three-parted, two-branched. Stigma color: Close to 53A. Seed/fruits: Seed and fruit development have not been observed.

Disease/pest resistance: Plants of the new *Tricyrtis* have not been observed to be resistant to pathogens and pests common to *Tricyrtis*.

Temperature tolerance: Plants of the new *Tricyrtis* have been observed to tolerate temperatures from −28° C. to 44° C.

It is claimed:

1. A new and distinct cultivar of *Tricyrtis* plant named 'Taipei Silk', as illustrated and described.

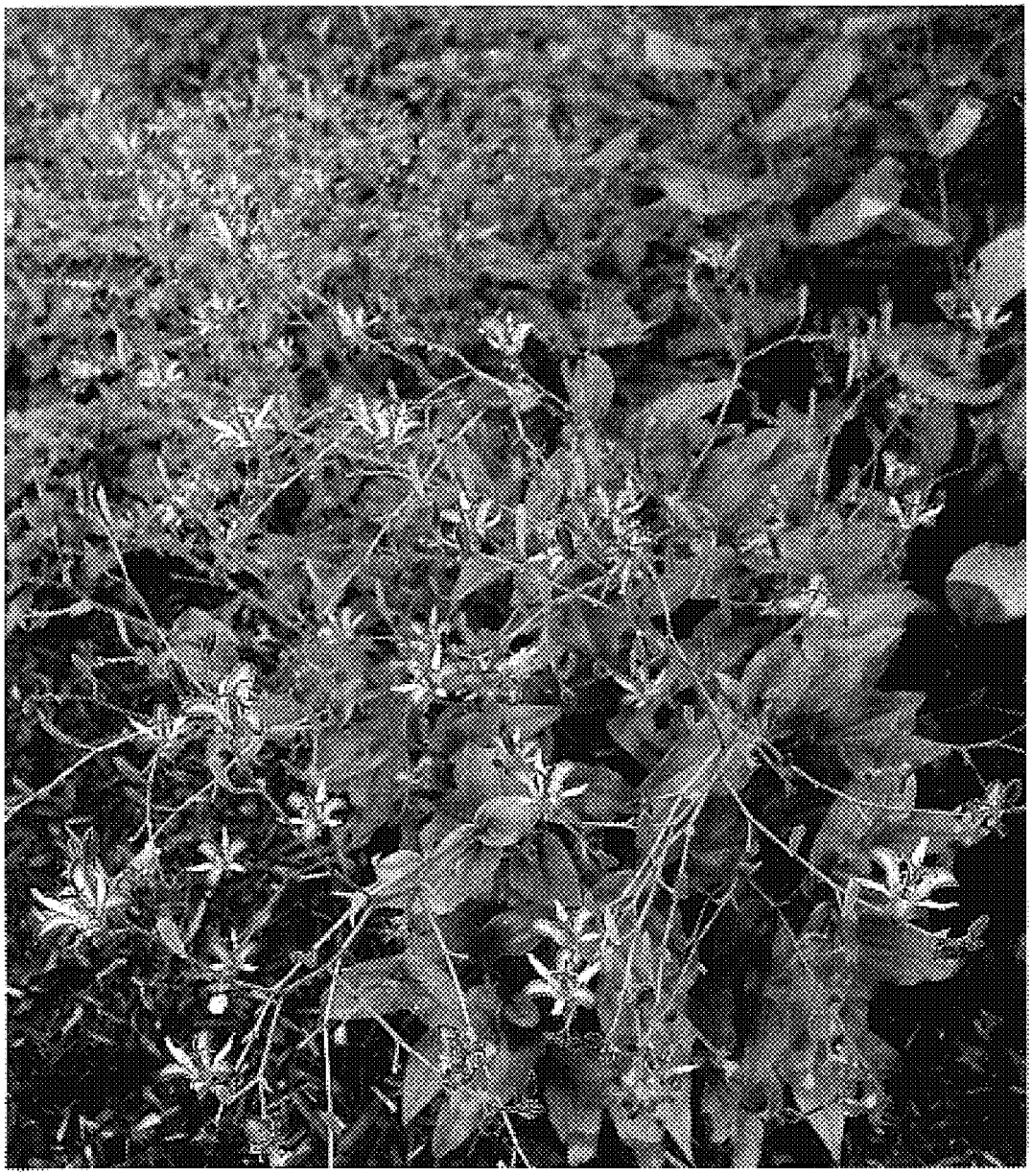

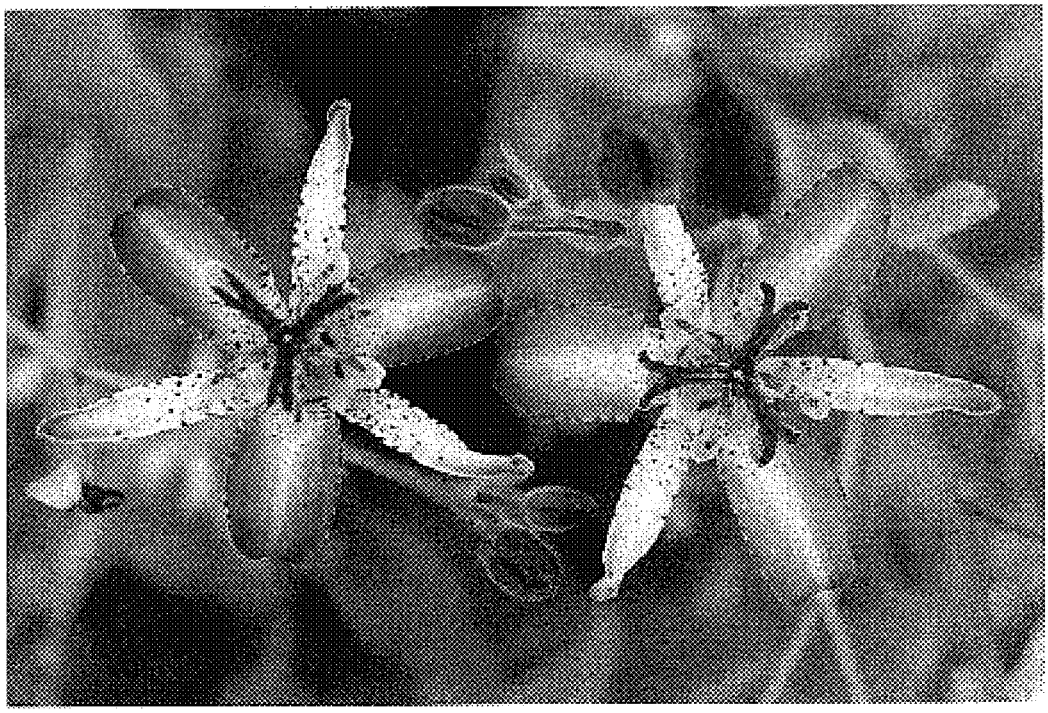

* * * * *